United States Patent [19]

Yorozu et al.

[11] Patent Number: 5,141,666
[45] Date of Patent: Aug. 25, 1992

[54] BATHING PREPARATION

[75] Inventors: Hidenori Yorozu, Tochigi; Kazuyuki Fukuda, Chiba; Yuji Ichii, Tochigi, all of Japan

[73] Assignee: Kao Corporation, Tokyo, Japan

[21] Appl. No.: 586,104

[22] Filed: Sep. 21, 1990

[30] Foreign Application Priority Data

Sep. 21, 1989 [JP] Japan .................. 1-246150

[51] Int. Cl.⁵ .............. C11D 17/00; C11D 7/06; C11D 7/12
[52] U.S. Cl. ............... 252/174.14; 252/157; 252/174.11; 252/DIG. 5
[58] Field of Search ........... 252/DIG. 5, 157, 174.11, 252/174.14

[56] References Cited

U.S. PATENT DOCUMENTS 4,210,550 7/1980 Cornelissens ............. 252/174.14

FOREIGN PATENT DOCUMENTS 0339276 11/1989 European Pat. Off. .
61-78717 4/1986 Japan .
62-45515 2/1987 Japan .
62-45516 2/1987 Japan .
2149511 6/1990 Japan .
2157705 10/1985 United Kingdom .

OTHER PUBLICATIONS

European Search Report.
Patent Abstracts of Japan, vol. 10, No. 252 (C-369)[2308], Aug. 29, 1986; & JP-A-61 078 717 (Asahi Chem. Ind.) Apr. 22, 1986.

Primary Examiner—A. Lionel Clingman
Assistant Examiner—William S. Parks
Attorney, Agent, or Firm—Sughrue, Mion, Zinn, Macpeak & Seas

[57] ABSTRACT

A bathing preparation comprising: (a) at least one carbonate; (b) at least one organic acid, wherein adipic acid amounts to 70% by weight or more of the total of the organic acid; and (c) at least one highly volatile perfume, is disclosed. The perfume is not vaporized into the air, thus the bathing preparation sustains its aroma in bath water for a prolonged period of time and exerts relaxing and refreshing bathing effects.

8 Claims, No Drawings

BATHING PREPARATION

FIELD OF THE INVENTION

This invention relates to a bathing preparation containing at least one organic acid and carbonate, characterized in that the vaporization of a perfume on dissolution of the bathing preparation in bath water, together with the bubbling of carbon dioxide gas is inhibited, thereby allowing the perfume to give its odor for a prolonged period of time.

BACKGROUND OF THE INVENTION

A bathing preparation, which generally comprises a mixture of inorganic salts such as mirabilite, borax, sulfur, sodium chloride and carbonates, together with various additives (for example, perfume, colorant, vegetable extract, organic acid etc.), would impart a preferable odor or color to bath water. Such a preparation would also accelerate the blood circulation by appropriately stimulating the skin to relieve fatigue and to promote metabolism. Among these bathing preparations, bubbling preparations comprising one or more carbonates, together with organic acids, would form bubbles of carbon dioxide gas in bath water thereby to give additional beneficial effects that enhance relaxation and refreshment provided by bathing.

In order to further improve the above-mentioned effects, a perfume is usually added to a bathing preparation. However, a problem encountered when using a highly volatile perfume is that the perfume is quickly vaporized, due to, e.g., the bubbling of carbon dioxide gas from the carbonates, which removes the beneficial effect of using the perfume.

Attempt to solve this problem include proposals in JP-A-62-223111 and JP-B-52-21573 to encapsulate, or include in a clathrate a perfume so as to prevent the vaporization of the perfume and achieve a sustained odor. (The term "JP-A" as used herein means an "unexamined published Japanese patent application" while the term "JP-B" as used herein means an "examined Japanese patent publication".) However encapsulation or clathrate inclusion requires a troublesome procedure and additional cost, which makes these methods economically disadvantageous. In addition to these economical disadvantages, it is difficult to form tablets of a bathing preparation comprising an encapsulated perfume.

SUMMARY OF THE INVENTION

Under these circumstances, we have conducted extensive studies in order to solve the above-mentioned problems. As a result, we have found out that the use of organic acids containing about 70% (by weight, the same will apply hereinafter) or more of adipic acid in a bathing preparation makes it possible to prevent the vaporization of a particular volatile perfumes without requiring any additional specific means, such as encapsulation or clathrate inclusion.

Accordingly, the present invention provides a bathing preparation comprising:

(a) at least one carbonate;

(b) at least one organic acid, wherein adipic acid amounts about 70% by weight or more of the total of the organic acids; and (c) at least one perfume selected from the group consisting of a terpene hydrocarbon having 10 carbon atoms and a formate, an acetate or a propionate of an alcohol having 5 to 10 carbon atoms.

DETAILED DESCRIPTION OF THE INVENTION

Examples of carbonates to be used in bathing preparations of the present invention include sodium hydrogencarbonate, sodium carbonate, potassium hydrogencarbonate, potassium carbonate, calcium carbonate, magnesium carbonate and sodium sesquicarbonate. These carbonates can be used either alone or a mixture thereof.

The content of the carbonate(s) can range from about 5 to about 80%, preferably from about 10 to about 50%, based on the total weight if the bathing preparation.

Organic acids to be contained in the bathing preparation of the present invention should comprise 70% or more of adipic acid. Examples of additional organic acids, useful for comprising the remaining portion of the organic acids, include citric acid, succinic acid, malic acid and tartaric acid. When the amount of adipic acid in the organic acid is less than about 70%, the vaporization of the above-mentioned highly volatile perfume cannot be prevented. The content of the organic acids may range from about 10 to about 80%, preferably from about 20 to about 50%, based on the total weight of the bathing preparation.

Adipic acid, which is hardly soluble in water, sometimes show floatation when dissolved in bath water. Therefore, adipic acid may be solubilized by surface-treatment with a water soluble polymer, e.g., sodium polyacrylate or sodium carboxymethyl cellulose, or a hydrophilic nonionic surfactant, e.g., polyethylene glycol, sucrose fatty acid ester or polyglycerol fatty acid ester or a combination thereof.

The highly volatile perfume herein means a perfume having a vapor pressure of 1 mmHg or more. Examples of such the highly volatile perfumes that can be used in the bathing preparation of the present invention include terpene hydrocarbons having 10 carbon atoms such as a-pinene, β-pinene, camphene, limonene, terpinolene, myrcene and p-cymene; formates of an alcohol having 5 to 10 carbon atoms such as geranyl formate, benzyl formate and phenylethyl formate; acetates of an alcohol having 5 to 10 carbon atoms such as isoamyl acetate, citronellyl acetate, geranyl acetate, benzyl acetate, linalyl acetate, phenylethyl acetate, menthyl acetate, bornyl acetate, terpenyl acetate, cinnamyl acetate, anisyl acetate and myrcenyl acetate; and propionates of an alcohol having 5 to 10 carbon atoms such as linalyl propionate, citronellyl propionate, geranyl propionate, benzyl propionate, terpenyl propionate and cinnamyl propionate.

Such a highly volatile perfume can be employed alone in the bathing preparation of the present invention, or alternately, it may be blended with at least one other perfume.

The content of volatile perfumes in the bathing preparation of the present invention can range from about 0.001 to about 2%, preferably from about 0.005 to about 0.6%, based on the total weight of the bathing preparation. The content of the total perfume composition can preferably range from about 0.2 to about 2% based on the total weight of the bathing preparation.

In addition to the above-mentioned components, the bathing preparation of the present invention can further comprise, for example, a sulfate, such as sodium sulfate, magnesium sulfate or zinc sulfate and a hydrochloride such as sodium chloride, potassium chloride and magnesium chloride.

Furthermore, the bathing preparation of the present invention may comprise commonly employed additives (for example, colorants, vitamins, components contained in hot spring water, proteases, algae extracts, sodium alginates, lanolin, silicones, herbs, herb extracts, etc.) to enhance benefits provided by bathing.

When the pH value of bathing water is adjusted to about 5 to about 7, by appropriately selecting the ratio of organic acids and carbonates present in the bathing preparation of the present invention, carbon dioxide gas can be present in the bath water in a dissolved state. The carbon dioxide gas dissolved in the bath water can give an additional effect, e.g., an increase in the blood circulation.

The bathing preparation of the present invention may be formulated into various forms in a manner as disclosed, for example, in EP-A 0 333 223. Preferably, the bathing preparation of the present invention is formulated into a tablet which makes it possible to improve the dissolution of carbon dioxide gas in bath water. However, such the bathing preparation can also be formulated into powders or granules. Upon formulation, fillers or lubricants may be further added, if desired.

As described above, the bathing preparation of the present invention, which comprises organic acids in which adipic acid amounts to 70% or more, can retain a particular highly volatile perfume within bath water for prolonged periods of time without being vaporized into the air, thus providing beneficial bathing effects.

To further illustrate the present invention, the following Examples will be given. Unless otherwise specified, all percents are by weight.

Table 1 summarizes perfumes A–K which are used in the following Examples.

TABLE 1

| Perfume Composition | A (%) | B (%) | C (%) | D (%) | E (%) | F (%) | G (%) | H (%) | I (%) | J (%) | K (%) |
|---|---|---|---|---|---|---|---|---|---|---|---|
| Limonene | 60 | | | | 40 | | | 52 | 40 | 70 | 8 |
| Pinene | 20 | | | | | | | | | 20 | |
| Terpinolene | 20 | | | | 10 | | | 10 | | | 1 |
| Geranyl formate | | 40 | | | 20 | | 30 | | 1 | 1 | |
| Benzyl formate | | 30 | | | | 10 | | | | | |
| Phenylethyl formate | | 30 | | | 30 | | | | | | |
| Citronellyl acetate | | | 20 | | | | 20 | 2 | | 1 | 3 |
| Geranyl acetate | | | 30 | | | | | | 5 | 1 | 3 |
| Benzyl acetate | | | 10 | | | 10 | 10 | | 1 | | |
| Phenylethyl acetate | | | 20 | | | 30 | | 4 | | | 1 |
| Terpenyl acetate | | | 20 | | | | | | | | 3 |
| Benzyl propionate | | | | 40 | | 50 | | | | 1 | 2 |
| Isoamyl propionate | | | | 10 | | | 40 | | | 2 | |
| Terpenyl propionate | | | | 50 | | | | | | | |
| Lilial | | | | | | | | | 10 | | 15 |
| Methyl dihydrojasmonate | | | | | | | | | | 10 | 10 |
| Cyclamen aldehyde | | | | | | | | 1 | | | 5 |
| Isoamyl salicylate | | | | | | | | | 2 | | |
| Methyl anthranilate | | | | | | | | 1 | | | 1 |
| Methyl methylanthranilate | | | | | | | | | 1 | | 1 |
| Methyl naphthyl Ether | | | | | | | | | 1 | | |
| Ethyl naphthyl Ether | | | | | | | | | 1 | | 1 |
| Tonalide | | | | | | | | | 4 | | |
| Pentalide | | | | | | | | 4 | | | 10 |
| Galaxolide | | | | | | | | 4 | 1 | 10 | 20 |
| Ethyl vanillin | | | | | | | | 0.1 | | 1 | |
| Anisaldehyde | | | | | | | | | | | 1 |
| Geraniol | | | | | | | | 5 | | | 8 |
| Anethole | | | | | | | | | | 2 | 1 |
| Phenyl ethyl alcohol | | | | | | | | 14.8 | 13 | | |
| Terpineol | | | | | | | | | 1 | | |
| Damascone | | | | | | | | 0.1 | | 0.5 | |
| Ionone | | | | | | | | 1 | | | 5 |
| Allylamyl glycolate | | | | | | | | | | 0.5 | |
| Cis-3-Hexenyl salicylate | | | | | | | | | | | 1 |

EXAMPLE 1

| | |
|---|---|
| Sodium Hydrogen Carbonate | 43.8 (%) |
| Sodium Carbonate | 15 |
| Organic Acids (specified in Table 2) | 40 |
| Dextrin | 0.8 |
| Perfume A | 0.4 |

A bathing preparation of the above composition was mixed and tabletted. Then 50 g of tablet of each bathing preparation was introduced with a bathtub (910×710 mm) filled with 150 l of water at 40° C. The odor of the bath water was organoleptically evaluated three times by ten skilled panelists, at various times intervals, based on the following criteria, and expressed in the major result thereof.

Criteria for Evaluation

A: Full smell.
B: Moderate smell.
C: Weak smell.
D: No smell.

However, it is to be noted here that criteria A and B mean an odor satisfactory as a bathing preparation.

Table 2 summarizes the results, wherein Products 1 to 4 are comparative examples and Products 5 to 8 are examples privided occording to the present invention.

TABLE 2

|  | Comparative Product | | | | Product of the Invention | | | |
|---|---|---|---|---|---|---|---|---|
|  | 1 (%) | 2 (%) | 3 (%) | 4 (%) | 5 (%) | 6 (%) | 7 (%) | 8 (%) |
| Organic Acid Composition | | | | | | | | |
| Succinic Acid | 100 | 80 | 60 | 40 | 30 | 20 | 0 | 0 |
| Adipic Acid | 0 | 20 | 40 | 60 | 70 | 80 | 100 | 70 |
| Tartaric Acid | 0 | 0 | 0 | 0 | 0 | 0 | 0 | 30 |
| Intensity of Odor | | | | | | | | |
| At disintegration | C | C | B | A | A | A | A | A |
| After 5 minutes | D | C | C | B | A | A | A | B |
| After 15 minutes | D | D | C | B | A | A | A | B |
| After 60 minutes | D | D | C | C | B | A | A | B |

EXAMPLE 2

| | |
|---|---|
| Sodium Hydrogencarbonate | 41.8 (%) |
| Sodium Carbonate | 15.0 |
| Organic Acids (specified in Table 3) | 40.0 |
| Dextrin | 0.8 |
| Polyethylene Glycol 6000 | 2.0 |
| Perfume A (specified in Table 3) | 0.4 |

A bathing preparation of the above composition was mixed and tabletted. Then each bathing preparation was introduced into a bathtub in the same manner as described in Example 1. The odor of the bath water was organoleptically evaluated by skilled panelists, similar to Example 1. Table 3 shows the results, wherein Product 9 is a comparative example and Products 10 to 15 are of the present invention.

In the production of the bathing preparation, the adipic acid had been passed through a sieve of 60 mesh and preliminarily treated by mixing with 0.03% of a sucrose fatty acid ester prior to the use in order to provide increased solubility of the adipic acid in water.

TABLE 3

|  | Comparative Product | Product of Invention | | | | | |
|---|---|---|---|---|---|---|---|
|  | 9 | 10 | 11 | 12 | 13 | 14 | 15 |
| Perfume | B | B | C | D | E | F | G |
| Organic acid Composition (%) | | | | | | | |
| Succinic acid | 90 | 30 | 30 | 30 | 30 | 20 | 20 |
| Adipic acid | 10 | 70 | 70 | 70 | 70 | 80 | 80 |
| Intensity of odor after 60 minutes | D | A | B | A | B | A | A |

A bathing preparation of the same composition as the one described in Example 2, except that the perfume specified in Table 4 was used, was mixed and tabletted. Then each bathing preparation was introduced into a bathtub in the same manner as described in Example 1. Similarly to Example 1, the odor of the bath water was organoleptically evaluated by skilled panelists. Table 4 shows the results wherein Product 16 is a comparative example and Products 17 to 20 are of the present invention.

TABLE 4

|  | Comparative Product | Product of the Invention | | | |
|---|---|---|---|---|---|
|  | 16 | 17 | 18 | 19 | 20 |
| Perfume | H | H | I | J | K |
| Organic acid | | | | | |

| Composition (%) | | | | | |
|---|---|---|---|---|---|
| Succinic acid | 100 | 30 | 30 | 30 | 30 |
| Adipic acid | 0 | 70 | 70 | 70 | 70 |
| Intensity of odor after 60 minutes | D | B | A | A | B |

While the invention has been described in detail and with reference to specific examples thereof, it will be apparent to one skilled in the art that various changes and modifications can be made therein without departing from the spirit and scope thereof.

What is claimed is:

1. A bathing preparation consisting essentially of
   (a) at least one carbonate;
   (b) at least one organic acid, wherein adipic acid amounts to 70% by weight or more of the total of the organic acid; and
   (c) at lest one highly volatile perfume selected from the group consisting of a terpene hydrocarbon having 10 carbon atoms, and a formate, an acetate or a propionate of an alcohol having 5 to 10 carbon atoms, wherein
      (i) said at least one carbonate is present in an amount of from about 5 to about 80% by weight based on the total weight of the bathing preparation;
      (ii) said at least one organic acid is present in an amount of from about 10 to about 80% by weight based on the total weight of the bathing preparation; and
      (iii) said at least one perfume is present in an amount of from about 0.001 to about 2.0% by weight based on the total weight of the bathing preparation;
   and wherein said highly volatile perfume is provided without encapsulating or clathrating, and whereby addition of said bathing preparation to water results in reduced evaporation of said volatile perfume from said water.

2. A bathing preparation as claimed in claim 1, wherein said at least one carbonate is present in an amount of from about 10 to about 50% by weight based on the total weight of the bathing preparation.

3. A bathing preparation as claimed in claim 1, wherein said at least one organic acid is present in an amount of from about 20 to about 50% by weight based on the total weight of the bathing preparation.

4. A bathing preparation as claimed in claim 1, wherein said at least one perfume is present in an amount of from about 0.005 to about 0.6% by weight based on the total weight of the bathing preparation.

5. A method of preventing loss of a volatile perfume from a bathing composition, without encapsulating or clathrating the perfume, comprising the steps of:

(1) providing a bathing preparation comprising a mixture of at least one carbonate, at least one organic acid wherein adipic acid amounts to 70% by weight or more of the total weight of the organic acid, and at least one perfume selected from the group consisting of a terpene hydrocarbon having 10 carbon atoms, and a formate, acetate or propionate of an alcohol having 5 to 10 carbon atoms, to form a bathing preparation; and (2) adding said bathing preparation into bath water, wherein (i) said at least one carbonate present in an amount of from about 5 to about 80% by weight based on the total weight of the bathing preparation;

(ii) said at least one organic acid is present in an amount of about 10 to about 80% by weight based on the total weight of the bathing preparation; and (iii) said at least one perfume is present in an amount of about 0.001 to about 2.0% by weight based on the total weight of the bathing preparation.

6. A method as claimed in claim 5, wherein said at least one carbonate is present in an amount of from about 10 to about 50% by weight based on the total weight of the bathing preparation.

7. A method as claimed in claim 5, wherein said at least one organic acid is present in an amount of about 20 to about 50% by weight based on the total weight of the bathing preparation.

8. A method as claimed in claim 5, wherein said at least one perfume is present in an amount of about 0.005 to about 0.6% by weight based on the total weight of the bathing preparation.

* * * * *